US00PP16139P3

(12) United States Plant Patent
de Groot

(10) Patent No.: US PP16,139 P3
(45) Date of Patent: Dec. 6, 2005

(54) HYBRID TEA ROSE PLANT NAMED 'RUIMZ15'

(50) Latin Name: *Rosa hybrida*
Varietal Denomination: RUIMZ15

(75) Inventor: Henk de Groot, De Kwakel (NL)

(73) Assignee: De Ruiter's Nieuwe Rozen, B.V., De Kwakel (NL)

( * ) Notice: Subject to any disclaimer, the term of this patent is extended or adjusted under 35 U.S.C. 154(b) by 162 days.

(21) Appl. No.: 10/341,893

(22) Filed: Jan. 13, 2003

(65) Prior Publication Data

US 2003/0135901 P1 Jul. 17, 2003

(30) Foreign Application Priority Data

Jan. 15, 2002 (EP) ..... 2001/2115

(51) Int. Cl.[7] ..... A01H 5/00

(52) U.S. Cl. ..... Plt./134

(58) Field of Search ..... Plt./134

(56) References Cited

U.S. PATENT DOCUMENTS

PP11,175 P * 1/2000 Pouw ..... Plt./137

OTHER PUBLICATIONS

UPOV ROM GTITM Computer Database, GTI Jouve Software 2003/05 Citations for 'Ruimz15'.*

* cited by examiner

*Primary Examiner*—Kent Bell
*Assistant Examiner*—W C Haas
(74) *Attorney, Agent, or Firm*—Christie, Parker & Hale, LLP

(57) ABSTRACT

A new and distinct hybrid tea rose plant having attractive large cream flowers.

1 Drawing Sheet

Botanical classification: *Rosa hybrida.*
Variety denomination: RUIMZ15.

BACKGROUND OF THE INVENTION

The present invention relates to a new and distinct variety of rose plant of the hybrid tea rose class, which was discovered in The Netherlands, in a controlled planting of 'RUILIRO' (U.S. Plant Pat. No. 11,175) as a natural branch mutation. The mutation was vegetatively propagated from cuttings by self-rooting and tested for productivity and growth. The varietal denomination of this new rose is named 'RUIMZ15'.

SUMMARY OF THE INVENTION

Among the novel characteristics possessed by this new variety which distinguishes it from its parent and all other varieties of which I am aware are its flower color.

Asexual reproduction by propagation of grafting of the new variety as performed in De Kwakel, The Netherlands shows that the foregoing and other distinguishing characteristics come true to form and are established and transmitted through succeeding propagation.

COMPARISON WITH PARENT

The new variety differs from its parent in flower color, inasmuch as the flowers of 'RUILIRO' are a pink blend and flowers of the new variety are cream.

BRIEF DESCRIPTION OF THE ILLUSTRATION

The accompanying illustration shows a typical specimen of the new variety depicted in color as nearly true as is reasonably possible to make the same in a color illustration of this character.

DESCRIPTION OF THE NEW VARIETY

The following is a detailed description of the new variety with color terminology in accordance with The Royal Horticultural Society Colour Chart (R.H.S.C.C.) from 1995. The terminology used in color description herein refers to plate numbers in the aforementioned color chart. Phenotypic expression may vary with light availability, environmental and cultural conditions.

The following observations are made of 9-month-old plants grown in a greenhouse in De Kwakel, The Netherlands during September from a cutting. The plants have grown in a substrate of cocopeat. The average temperature is 19° C. and there was an assimilation light of 6000 Lux.

In all respects other than characteristics of the flower, plants of the new variety are the same as of 'RUILIRO'.

FLOWER

Blooming habit: Nearly continuous.

A. Bud:

(*1*) *Size.*—About 5 cm long by about 2 to 4 cm wide, before sepals fall. About 5 to 6 cm long by about 4 cm wide, after sepals separate further.

(*2*) *Form.*—Ovate (shape of longitudinal section just before separation of sepals); urn-shaped after sepals part and petals begin to separate.

(*3*) *Color.*—Before sepals separate, white to near 56D with deeper tone, near 55C at petal edge becoming lighter until becoming near 4D at point of petal attachment.

(4) *Sepals.*—One to three are longer than bud, most very foliaceous; near 147A on top surface, lighter, near 147B, on undersurface.

(5) *Peduncle.*—Long: Strength-erect, strong. Color near 138A to 138B.

B. Flower: Medium; viewed from side — (a) upper part of fully opened flower, convex; (b) lower part of fully opened flower, concave.

(1) *Size.*—Average size when fully expanded — about 7 to 9 cm at about full open.

(2) *Borne.*—Singly, one to a stem.

(3) *Form.*—Mainly spiral imbricated, some outer petals have pointed apices, some inner petals ruffled and some roll under; somewhat recessed center in open bloom.

(4) *Petalage.*—Fully double, about 23.

(5) *Color.*—After sepals part and petals unfurl, color of petal top surface near edges is near 8D. Petals undersurface exhibits same coloration as top surface. Color at point of petal attachment is near 2B.

(6) *Peduncle.*—Generally smooth.

(7) *Fragrance.*—Absent or weak.

(8) *Length of stems.*—About 60 cm to 100 cm.

Petals:

(1) *Texture.*—Crisp.

(2) *Appearance.*—Inside velvety and outside satiny.

(3) *Form and size.*—Broad, medium, medium undulation of margin.

(4) *Arrangement.*—Regularly arranged, imbricated.

(5) *Petaloids.*—Several, about 2 to 5.

(6) *Lasting quality.*—Long-lasting quality on plant (about 20 days) and after cutting (about 14 days).

REPRODUCTIVE ORGANS

A. Stamens, filaments and anthers:

*Arrangement and color.*—Regularly arranged around styles; color of filaments — white to pale yellow.

B. Pollen color: Near 19B to 19C.

C. Styles: Long, stigma above mouth of receptacle, white.

D. Stigmas: Yellow.

E. Hip: Pitcher-shaped; small seed vessel at petal fall.

PLANT

A. Form: Narrow, bushy, average disease resistance; height about 1.5 m, spread about 0.5 m.

B. Growth: Vigorous.

C. Foliage: Compound 3, 5 and 7 leaflets.

(1) *Size.*—3-leaflet leaf, terminal leaflet about 7 cm long; 5-leaflet leaf, terminal leaflet about 5 to 6 cm long; 7-leaflet leaf, terminal leaflet about 5 to 6 cm long.

(2) *Quantity.*—Abundant.

(3) *Color.*—Juvenile foliage — top near 187A underside grey brown near 187B; absent or weak anthocyanin coloration, (shoot about 20 cm long); mature top leaf color — near 137A; undersurface near 138B.

(4) *Shape.*—Broad oval.

(5) *Texture.*—Upper side is medium glossy; underside is matte.

(6) *Edge.*—Serrate.

(7) *Serration.*—Serrulate, obtuse apices.

(8) *Leaf stem.*—Color — near 138B.

(9) *Stipules.*—About 1.8 cm, green color same as leaves.

(10) *Leaflets.*—Cross section — flat; weak undulation of margin; terminal leaflet — medium length and medium width; rounded base.

D. Wood:

(1) *New wood.*—Color — young shoots have medium anthocyanin; coloration — bronze to reddish brown, near 187B.

(2) *Old wood.*—Color — green, near 137C.

E. Prickles (thorns):

(1) *Prickles.*—Present; quantity few on lower part, top ⅓ no prickles; shape of lower side — concave, near 138C, on new shoots about 4 prickles between internodes, near 187C; short prickles absent or very few, long prickles few. Position — irregular when they appear.

I claim:

1. A new and distinct hybrid tea rose plant having attractive large cream flowers.

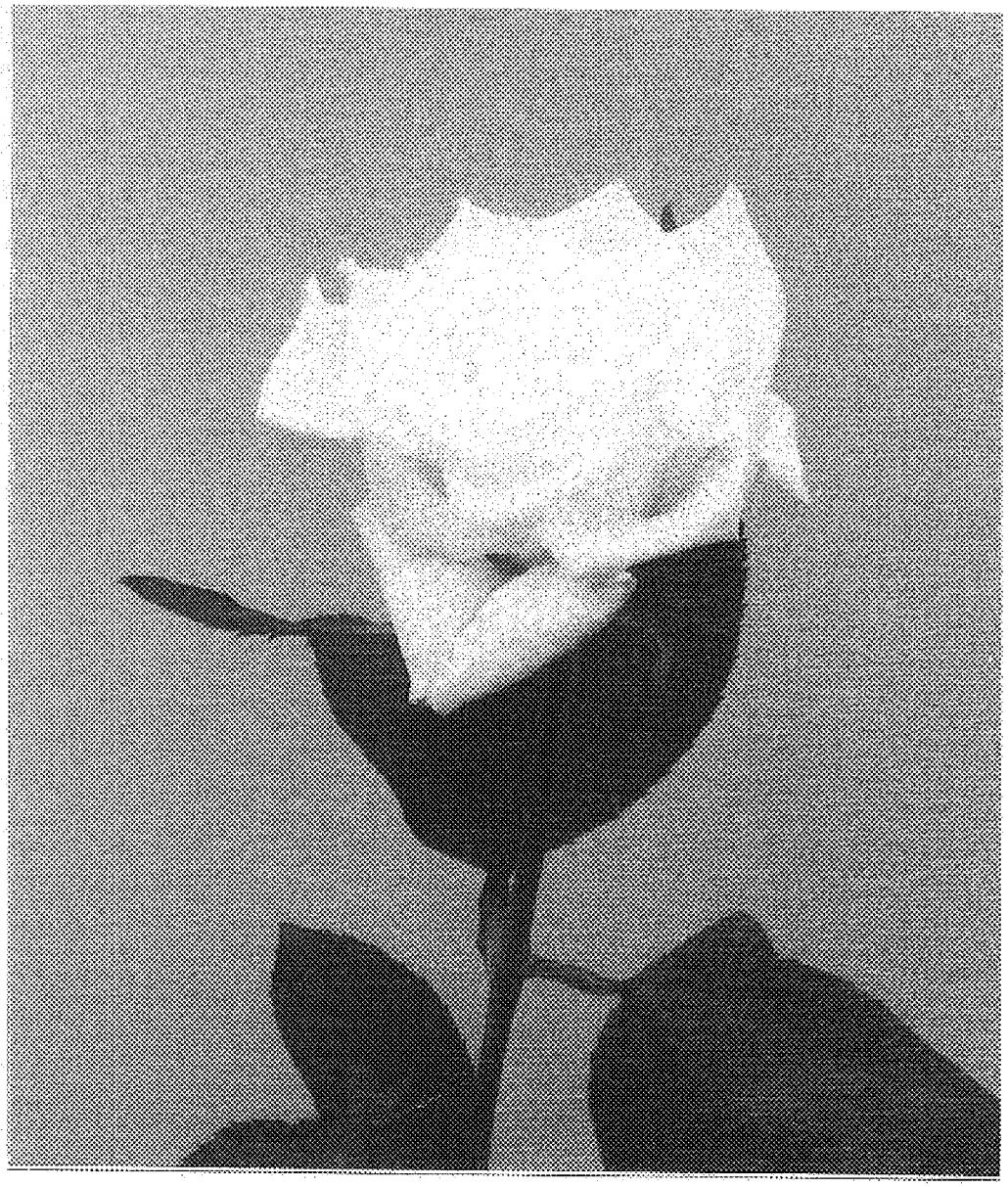

* * * * *